US009689826B2

(12) United States Patent
Haick et al.

(10) Patent No.: US 9,689,826 B2
(45) Date of Patent: Jun. 27, 2017

(54) DETECTION OF CHRONIC KIDNEY DISEASE AND DISEASE PROGRESSION

(71) Applicant: Technion Research and Development Foundation Ltd., Haifa (IL)

(72) Inventors: Hossam Haick, Haifa (IL); Ophir Marom, Zichron Yaacov (IL)

(73) Assignee: Technion Research and Development Foundation Ltd., Haifa (IL)

( * ) Notice: Subject to any disclaimer, the term of this patent is extended or adjusted under 35 U.S.C. 154(b) by 524 days.

(21) Appl. No.: 13/793,833

(22) Filed: Mar. 11, 2013

(65) Prior Publication Data

US 2013/0236981 A1 Sep. 12, 2013

Related U.S. Application Data

(60) Provisional application No. 61/609,319, filed on Mar. 11, 2012.

(51) Int. Cl.
*G01N 33/497* (2006.01)
*G01N 27/26* (2006.01)
*G01N 27/06* (2006.01)

(52) U.S. Cl.
CPC ............ *G01N 27/26* (2013.01); *G01N 27/06* (2013.01); *G01N 33/497* (2013.01); *G01N 2800/347* (2013.01)

(58) Field of Classification Search
CPC .... G01J 1/04; G01J 1/0411; G01J 5/02; G01J 5/024; G01J 5/045; G01J 5/08; G01J 5/0803; G01J 5/0806; G01J 2005/068; G01J 5/0846; G01J 5/0225; G01J 5/06; G01J 5/089; G01J 5/04; G01J 5/10; B82Y 30/00; G01N 27/4146; G01N 33/497; G01N 27/127; G01N 27/4141; G01N 33/587; G01N 2033/4975; G01N 2800/50; A61K 47/48884; A61K 47/48907; A61K 9/51

See application file for complete search history.

(56) References Cited

U.S. PATENT DOCUMENTS

| | | | |
|---|---|---|---|
| 6,312,390 | B1 | 11/2001 | Phillips |
| 6,411,905 | B1 | 6/2002 | Guoliang et al. |
| 6,589,748 | B2 | 7/2003 | Comper |
| 6,606,566 | B1 | 8/2003 | Sunshine |

(Continued)

FOREIGN PATENT DOCUMENTS

| | | |
|---|---|---|
| WO | 2008039165 A2 | 4/2008 |
| WO | 2008052104 A2 | 5/2008 |

(Continued)

OTHER PUBLICATIONS

American Thoracic Society (ATS) and the European Respiratory Society (ERS)., ATS/ERS recommendations for standardized procedures for the online and offline measurement of exhaled lower respiratory nitric oxide and nasal nitric oxide, 2005. Am J Crit Care Med 171(8): 912-930.

(Continued)

*Primary Examiner* — Yelena G Gakh
(74) *Attorney, Agent, or Firm* — Roach Brown McCarthy & Gruber, P.C.; Kevin D. McCarthy (57) ABSTRACT

The present invention provides a sensor or a system comprising gold nanoparticles coated with specific organic coatings for diagnosing, staging or monitoring chronic kidney disease.

12 Claims, 4 Drawing Sheets

(56) References Cited

U.S. PATENT DOCUMENTS

| | | |
|---|---|---|
| 6,609,068 B2 | 8/2003 | Cranley et al. |
| 6,620,109 B2 | 9/2003 | Hanson, III |
| 6,767,732 B2 | 7/2004 | Alocilja et al. |
| 6,773,926 B1 | 8/2004 | Freund et al. |
| 6,820,012 B2 | 11/2004 | Sunshine |
| 6,839,636 B1 | 1/2005 | Sunshine et al. |
| 6,841,391 B2 | 1/2005 | Lewis et al. |
| 7,052,854 B2 | 5/2006 | Melker et al. |
| 7,076,371 B2 | 7/2006 | Fu |
| 7,138,229 B2 | 11/2006 | Hu et al. |
| 7,153,272 B2 | 12/2006 | Talton |
| 7,547,931 B2 | 6/2009 | Star et al. |
| 8,366,630 B2 | 2/2013 | Haick et al. |
| 2002/0117659 A1 | 8/2002 | Lieber et al. |
| 2005/0054942 A1 | 3/2005 | Melker et al. |
| 2006/0034731 A1* | 2/2006 | Lewis ............... G01N 27/121 422/88 |
| 2007/0048180 A1 | 3/2007 | Gabriel et al. |
| 2007/0106168 A1 | 5/2007 | O'Neil et al. |
| 2008/0021339 A1 | 1/2008 | Gabriel et al. |
| 2010/0273665 A1 | 10/2010 | Haick et al. |
| 2011/0098591 A1 | 4/2011 | Haick et al. |

FOREIGN PATENT DOCUMENTS

| | | |
|---|---|---|
| WO | 2009066293 A1 | 5/2009 |
| WO | 2009144725 A1 | 12/2009 |
| WO | 2010064239 A1 | 6/2010 |
| WO | 2010079490 A1 | 7/2010 |

OTHER PUBLICATIONS

Amorim LC and de L Cardeal Z (2007) Breath air analysis and its use as a biomarker in biological monitoring of occupational and environmental exposure to chemical agents. J Chromatogr B Analyt Technol Biomed Life Sci 853(1-2): 1-9.

Aspnes DE and Theeten JB (1980) Spectroscopic analysis of the interface between Si and its thermally grown oxide. J Electrochem Soc 127(6): 1359-1365.

Brust M et al., (1994) Synthesis of thiol-derivatised gold nanoparticles in a two-phase Liquid-Liquid system. J Chem Soc Chem Commun 801-802.

Buszewski B et al., (2007) Human exhaled air analytics: biomarkers of diseases. Biomed Chromatogr 21(6): 553-566.

Cao W and Duan Y (2007) Current status of methods and techniques for breath analysis. Critical Reviews in Analytical Chemistry 37(1): 3-13.

Chen X et al., (2005) A study of an electronic nose for detection of lung cancer based on a virtual SAW gas sensors array and imaging recognition method. Measurement Science and Technology 16(8): 1535-1546.

Collins AJ et al., (2003) Chronic kidney disease and cardiovascular disease in the Medicare population. Kidney Int Suppl. 87: S24-S31.

Cortes C and Vapnik V (1995) Support-vector networks. Mach Learn 20(3): 273-297.

Devarajan P (2010) Review: Neutrophil gelatinase-associated lipocalin: A troponin-like biomarker for human acute kidney injury. Nephrology 15(4): 419-428.

Di Natale et al., (1999) Electronic nose analysis of urine samples containing blood. Physiol Meas 20(4): 377-384.

Dovgolevsky E and Haick H (2008) Direct observation of the transition point between quasi spherical and cubic nanoparticles in two step seed mediated growth method. Small 4(11): 2059-2066.

Dovgolevsky E et al., (2009) Chemically Sensitive Resistors Based on Monolayer-Capped Cubic Nanoparticles: Towards Configurable Nanoporous Sensors. Small 5(10): 1158-1161.

Dovgolevsky E et al., (2010) Monolayer-Capped Cubic Platinum Nnoparticles for Sensing Nonpolar Analyst in Highly Humid Atmospheres. J Phys Chem C 114(33): 14042-14049.

Fend et al., (2004) Monitoring haemodialysis using electronic nose and chemometrics. Biosens Bioelectron 19(2): 1581-1590.

Gelperin A and Johnson ATC (2008) Nanotube-based sensor arrays for clinical breath analysis. J Breath Res 2(3): 037015 (6 pages).

Gordon S et al., (2002) Volatile organic compounds as breath biomarkers for active and passive smoking. Environ Health Perspect 110(7): 689-698.

Groves W et al., (1998) Analysis organic vapors in exhaled breath using a surface acoustic wave sensor array with preconcentration: selection and characterization of the preconcentrator adsorbent. Analytica Chimica Acta 371(2-3): 131-143.

Haick H (2007) Chemical Sensors Based Molecularly Modified Metallic Nanoparticles. J Phys D 40: 7173-7186.

Haick H et al., (2009) Sniffing chronic renal failure in rat model by an array of random networks of single-walled carbon nanotubes. ACS Nano 3(5): 1258-1266.

Hall M et al., (2009) The WEKA data mining software: an update. SIGKDD Explorations 11 (1): 10-18.

Hostetler MJ et al., (1998) Alkanethiolate Gold Cluster Molecules with Core Diameters from 1.5 to 5.2 nm: Core and Monolayer Properties as a Function of Core Size. Langmuir, 14: 24.

Jourde-Chiche N et al., (2009) Protein-bound toxins-update. Semin Dial 22: 334-339.

Kastler M et al., (2005) Influence of alkyl substituents on the solution- and surface-organization of hexa-peri-hexabenzocoronenes. J Am Chem Soc 127(12): 4286-4296.

Kuzmych O et al., (2007) Carbon nanotube sensors for exhaled breath components. Nanotechnology 18(37): 375502 (7 pages).

Lee CY and Strano MS (2008) Amine basicity (pKb) controls the analyte binding energy on single walled carbon nanotube electronic sensor arrays. J Am Chem Soc.130(5): 1766-1773.

Lee Y and Kim J (2007) Simultaneous electrochemical detection of nitric oxide and carbon monoxide generated from mouse kidney organ tissues. Anal Chem 79(20): 7669-7675.

Levey AS et al., (2005) Definition and classification of chronic kidney disease: a position statement from Kidney Disease: Improving Global Outcomes (KDIGO). Kidney Int 67(6): 2089-2100.

Lin et al., (2001) Application of the electron nose for uremia diagnosis. Sens Actuators B 76: 177-180.

Lu Y et al., (2006) A carbon nanotube sensor array for sensitive gas discrimination using principal component analysis. Journal of Electroanalytical Chemistry 593(1-2): 105-110.

Mashiach E et al., (1998) Renal ischemia-reperfusion injury: contribution of nitric oxide and renal blood flow. Nephron 80(4): 458-467.

Mazzone PJ (2008) Progress in the development of a diagnostic test for lung cancer through the analysis of breath volatiles. J Breath Res 2(3): 037014.

Mazzone PJ et al., (2007) Diagnosis of lung cancer by the analysis of exhaled breath with a colorimetric sensor array. Thorax 62(7): 565-568.

Meyer TW and Hostetter TH (2007) Uremia. N Engl J Med 357: 1316-1325.

Moorhead KT et al., (2011) Modelling acute renal failure using blood and breath biomarkers in rats. Comput. Methods Programs Biomed 101(2): 173-182.

O'sullivan CK and Guilbault GG (1999) Commercial quartz crystal microbalances—theory and applications. Biosensors and Bioelectronics 14(8-9): 663-670.

Ouyang G and Pawliszyn J (2006) SPME in environmental analysis. Anal Bioanal Chem 386(4): 1059-1073.

Parikh K et al., (2006) Flexible vapour sensors using single walled carbon nanotubes. Sensors and Actuators B: Chemical 113(1): 55-63.

Paska Y et al., (2011) Enhanced sensing of nonpolar volatile organic compounds by silicon nanowire field effect transistors. ACS Nano 5(7): 5620-5626.

Peng et al., (2008) Detecting simulated patterns of lung cancer biomarkers by random network of single walled carbon nanotubes coated with nanopolymeric organic materials. Nano Lett 8(11): 3631-3635.

(56) References Cited

OTHER PUBLICATIONS

Peng G et al., (2009) Detection of nonpolar molecules by means of carrier scattering in random networks of carbon nanotubes: toward diagnosis of diseases via breath samples. Nano Lett 9(4): 1362-1368.

Peng G et al., (2009) Diagnosing lung cancer in exhaled breath using gold nanoparticles. Nat Nanotechnol 4(10): 669-73.

Peng S et al., (2010) Detection of Lung, Breast, Colorectal and Prostate Cancers from Exhaled Breath Using a Singel Array of Nanosensors. Br J Cancer 103: 542-551.

Qi et al., (2003) Toward large arrays of multiplex functionalized carbon nanotube sensors for highly sensitive and selective molecular detection. Nano Letters 3(3): 347-351.

Simenhoff et al., (1977) Biochemical profile or uremic breath. N Engl J Med 297: 132-135.

Tisch U and Haick H (2010) Nanomaterials for Cross-Reactive Sensor Arrays. MRS Bull (35): 797-803.

Tisch U and Haick H (2011) Arrays of chemisensitive monolayer-capped metallic nanoparticles for diagnostic breath testing. Rev Chem Eng 26: 171-179.

Toda K et al., (2006) Measurement of ammonia in human breath with a liquid-film conductivity sensor. Anal Chem 78(20): 7284-7291.

Vanholder R et al., (2008) A bench to bedside view of uremic toxins. J Am Soc Nephrol 19: 863-870.

Voss et al., (2005) Smelling renal dysfunction via electronic nose. Ann Biomed Eng 33(5): 656.

Wang HT et al., (2007) Electrical detection of kidney injury molecule-1 with AlGaN/GaN high electron mobility transistors. Applied Physics Letters 91: 222101-222103.

Yu H et al., (2003) Detection volatile organic compounds in breath as markers of lung cancer using a novel electronic nose. Sensors, Proceedings of IEEE 2: 1333-1337.

Zhao et al., (1997) Soft lithographic methods for nano fabrication. J Mater Chem 7: 1069-1074.

Zilberman Y et al., (2009) Sponge-like structures of hexa-peri-hexabenzocoronenes derivatives enhances the sensitivity of chemiresistive carbon nanotubes to nonpolar volatile organic compounds. Langmuir 25(9): 5411-5416.

Marom O., Nakhoul F., Tisch U., Shiban A., Abassi Z. and Haick H., "Gold nanoparticle sensors for detecting chronic kidney disease and disease progression"; Nanomedicine (Lond). May 2012; 7(5):639-50 (12 pages).

* cited by examiner

DETECTION OF CHRONIC KIDNEY DISEASE AND DISEASE PROGRESSION

FIELD OF THE INVENTION

The present invention relates to a sensor, a system comprising a sensor array and methods of use thereof for diagnosing, staging and monitoring chronic kidney disease.

BACKGROUND OF THE INVENTION

Chronic kidney disease (CKD) is characterized by the progressive loss of kidney function over a period of months or years. Recent professional guidelines classify the severity of CKD according to the reduction in glomerular filtration rate (GFR). Stage 1 CKD is the mildest disease condition which is accompanied by few symptoms and stage 5 CKD is the most severe disease condition which is characterized by poor life expectancy when remained untreated (NKF KDOQI GUIDELINES, 2002; Levey et al., Kidney Int. 67(6), 2089-2100, 2005; and Collins et al., Kidney Int. Suppl. 87, S24-S31, 2003). Untreated CKD may further progress into end stage disease wherein endogenous kidney function is irreversibly lost, a condition which renders the patient dependent upon dialysis or kidney transplantation. Approximately 90% of end stage renal disease is attributed to untreated CKD.

Early detection of kidney dysfunction is essential for the proper treatment of CKD and can prevent the progression of uremia which is a state of systemic poisoning due to the progressive loss of kidney function. In healthy population, "uremic" toxins are normally excreted by the kidneys. In CKD patients, the filtration of kidney nepgrons (assessed by the glomerular filtration rate (GFR)) diminishes thus causing an accumulation of "uremic" toxins, which are retained in the blood. Over 5000 potential toxins were found to be associated with the loss of kidney function including phenols, indoles, skatoles, pyridine derivatives, polyamines, aliphatic and aromatic amines, hippurate esters, hormones (e.g. prolactin), trace elements (e.g., aluminum, vanadium, arsenic, and zinc), guanidine compounds, serum proteases, and $\beta$2-microglobulin (Vanholder et al., J. Am. Soc. Nephrol. 19(5), 863-870, 2008; Jourde-Chiche et al., Semin. Dial. 22(4), 334-339, 2009; and Meyer et al., N. Engl. J. Med. 357(13), 1316-1325, 2007).

Currently used markers for loss of kidney function are retained urea and creatinine levels in urine and blood samples. However, serum creatinine levels vary widely with age, gender, diet, muscle mass, muscle metabolism, medications, and hydration status (Devarajan, Nephrology 15(4), 419-428, 2010). Moreover, up to 60% of kidney function may be lost before serum creatinine levels begin to rise. These limitations, and the asymptomatic onset of the disease, contribute to delayed diagnosis and treatment of CKD.

Di Natale et al. (Physiol. Meas. 20, 377-384, 1999) disclosed the use of an electronic nose to analyze the headspace of urine samples for detecting blood contents and measuring the pH and the specific weight of the samples. Fend et al. (Biosens. Bioelectron. 19(2), 1581-1590, 2004) disclosed the use of an electronic nose comprising an array of 14 conducting polymer sensors together with principal component analysis and hierarchical cluster analysis to analyze blood samples for monitoring dialysis.

A novel approach that overcomes many constraints of the conventional diagnostic techniques relies on patterns of volatile biomarkers in exhaled breath. Some of the volatile organic compounds (VOCs) from plasma CKD biomarkers or their metabolic products, are transmitted to the alveolar exhaled breath through exchange via the lung, even at the onset of the disease. At later stages, the characteristic VOCs are responsible for the fishy smell often detected in the breath of advanced CKD patients (Simenhoff et al., N. Engl. J. Med. 297(3), 132-135, 1977).

Moorhead et al. (Comput. Methods Programs Biomed. 101(2) 173-182, 2011) disclosed a two-compartment model for estimating glomerular filtration and further disclosed the use of selected ion flow tube-mass spectrometry (SIFT-MS) for monitoring of breath analytes to determine renal function.

Breath analysis for the diagnosis of uremia using an electronic nose device was demonstrated by Lin et al. (Sens. & Actuat. B, 76, 177-180, 2001). A sensor module composed of six 12 MHz AT-cut quartz crystals array coated with probe peptides designed by simulating the olfactory receptor protein docking with target gas molecules in combination with discriminating analysis, were used. Breath analysis of normal subjects, patients with uremia, patients with chronic renal insufficiency (CRI) and patients with chronic renal failure (CRF) provided discrimination with a correct classification of 86.78%.

Voss et al. (Ann. Biomed. Engin., 33(5), 656, 2005) disclosed the application of an electronic nose system based on doped semiconductor metal oxide gas sensors for studying human body odor in patients with different stages of renal insufficiency. Principle component analysis (PCA) followed by quadratic discriminant analysis produced discrimination of all healthy subjects from renal patients and further discrimination of dialysis patients from patients with chronic renal failure with a correct classification of 95.2% for two principle odor components and 98.4% for three principle odor components.

Haick and co-workers have recently demonstrated the ability of an array of carbon-nanotube-based sensors to differentiate between healthy states and induced end stage renal disease in rats via breath samples, using a model of bilateral nephrectomy, and have achieved a success rate of over 95% (Haick et al., ACS Nano 3(5), 1258-1266, 2009).

WO 2010/064239 to one of the inventors of the present invention discloses a system comprising an array of sensors of single-walled carbon nanotubes (SWCNTs) coated with functionalized oligomers or polymers for measuring VOCs as biomarkers for diagnosis, prognosis and monitoring of renal insufficiencies including, acute renal failure and chronic renal failure.

At present, no simple and reliable technique is available for early diagnosis of CKD and monitoring disease progression through breath analysis. There thus remains an unmet need for diagnosing early stage CKD in a non-invasive manner suitable for population screening in non-specialist settings.

SUMMARY OF THE INVENTION

The present invention provides a sensor or an array of sensors comprising organically functionalized gold nanoparticles for the identification of early stage CKD, and the staging and monitoring of CKD disease progression.

The present invention provides a simple and reliable diagnosis of CKD suitable for large-scale screening of the population in non-specialist clinic. The tailored sensors of the present invention provide the detection of the onset of CKD prior to the appearance of clinical symptoms and the staging and monitoring of CKD progression thus allowing better management of the disease.

According to one aspect, the present invention provides a sensor for diagnosing, staging or monitoring CKD, the sensor comprising gold nanoparticles capped with an organic coating selected from the group consisting of 2-ethylhexanethiol, tert-dodecanethiol, hexanethiol and dibutyl disulfide. Each possibility represents a separate embodiment of the present invention. In one embodiment, the sensor of the present invention is sensitive to at least one volatile organic compound that is indicative of chronic kidney disease thereby providing the diagnosis, staging or monitoring of chronic kidney disease.

In another aspect, the present invention provides a system for diagnosing, staging or monitoring CKD, the system comprising (a) a sensor array comprising a plurality of sensors, wherein each sensor comprises gold nanoparticles capped with an organic coating selected from the group consisting of 2-ethylhexanethiol, tert-dodecanethiol, hexanethiol and dibutyl disulfide; (b) a detection means; and (c) a processing unit comprising a pattern recognition analyzer wherein the pattern recognition analyzer receives sensor output signals and compares them to stored data. In one embodiment, each sensor in the sensor array is sensitive to at least one volatile organic compound that is indicative of chronic kidney disease thereby providing the diagnosis, staging or monitoring of chronic kidney disease.

In some embodiments, the gold nanoparticles have a morphology selected from a cubic, a spherical, and a spheroidal morphology. Each possibility represents a separate embodiment of the present invention.

In other embodiments, the gold nanoparticles have a spherical morphology with diameters ranging from about 2 nm to about 5 nm.

In certain embodiments, the sensor is configured in a form selected from the group consisting of a capacitive sensor, a resistive sensor, an impedance sensor, and a field effect transistor sensor. Each possibility represents a separate embodiment of the present invention. In specific embodiments, the sensor is configured as a chemiresistive sensor (a chemiresistor).

In some embodiments, the system comprises four sensors comprising gold nanoparticles capped with an organic coating, each of the four sensors is capped with a different organic coating selected from the group consisting of 2-ethylhexanethiol, tert-dodecanethiol, hexanethiol and dibutyl disulfide.

In other embodiments, the detection means comprises a device for measuring changes in resistance, conductance, alternating current (AC), frequency, capacitance, impedance, inductance, mobility, electrical potential, optical property or voltage threshold. Each possibility represents a separate embodiment of the present invention.

In further embodiments, the pattern recognition analyzer comprises at least one algorithm selected from the group consisting of artificial neural network algorithm, support vector machine (SVM), principal component analysis (PCA), multi-layer perception (MLP), generalized regression neural network (GRNN), fuzzy inference system (FIS), self-organizing map (SOM), radial bias function (RBF), genetic algorithm (GAS), neuro-fuzzy system (NFS), adaptive resonance theory (ART), partial least squares (PLS), multiple linear regression (MLR), principal component regression (PCR), discriminant function analysis (DFA), linear discriminant analysis (LDA), cluster analysis, and nearest neighbor. Each possibility represents a separate embodiment of the present invention. In one embodiment, the at least one algorithm is support vector machine (SVM).

In another embodiment, the sensor or system of the present invention is useful for diagnosing, staging or monitoring CKD in a subject.

In various embodiments, the present invention provides a method of diagnosing, staging or monitoring chronic kidney disease in a subject, the method comprising exposing a sensor comprising gold nanoparticles capped with an organic coating selected from the group consisting of 2-ethylhexanethiol, tert-dodecanethiol, hexanethiol and dibutyl disulfide to a test exhaled breath sample and measuring a signal generated by at least one volatile organic compound that is indicative of chronic kidney disease in the test sample thereby providing the diagnosis, staging or monitoring of chronic kidney disease.

In some embodiments, the method comprises comparing the signal obtained from the test sample with the signal obtained from a control sample whereby a significant difference between the signal of the test sample and the signal of the control sample is indicative of chronic kidney disease or its stage.

In other embodiments, the signal comprises a plurality of response induced parameters that form a response pattern. In accordance with these embodiments, the signal is analyzed using a pattern recognition algorithm by comparing it to a response pattern obtained from a control sample whereby a significantly different response pattern of the test sample as compared the control sample is indicative of chronic kidney disease or its stage.

In certain embodiments, the present invention provides a method for diagnosing, staging and monitoring CKD in a subject, the method comprising the steps of: a) providing a sensor or a system as disclosed herein; (b) exposing the sensor or sensor array to a test exhaled breath sample; (c) measuring a plurality of response induced parameters or a plurality of signals generated by at least one volatile organic compound that is indicative of chronic kidney disease in the test sample from the sensor or sensor array using a detection means to obtain a response pattern; and (d) analyzing the response pattern obtained in step (c) using a pattern recognition algorithm by comparing it to a response pattern obtained from a control sample whereby a significantly different response pattern of the test sample as compared the control sample is indicative of CKD or its stage.

In some embodiments, the method for diagnosing, staging and monitoring CKD in a subject further provides the differentiation between subjects having CKD and healthy subjects, subjects having CKD and subjects having acute renal failure, or subjects having early or advanced stage CKD and subjects having end stage renal disease. In further embodiments, the method of diagnosing, staging and monitoring CKD further provides the differentiation between subjects having early stage CKD (stages 2-3), subjects having advanced stage CKD (stage 4) and subjects having end stage renal disease (stage 5).

In other embodiments, the methods of the present invention further comprise the step of concentrating the test exhaled breath sample prior to its measurement using at least one of a breath concentrator and a dehumidifying unit. Each possibility represents a separate embodiment of the present invention.

In certain embodiments, the response is formed by the sensor or sensor array detection of at least one volatile organic compound that is indicative of CKD. In particular embodiments, the at least one volatile organic compound (biomarker) that is indicative of CKD is selected from the group consisting of ethylene glycol, acetoin, styrene, toluene, isoprene, acetone, 2,2,6-trimethyl-octane, 2-butanone, and 2,4-dimethyl-heptane. Each possibility represents a separate embodiment of the present invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 1A-1B. Identification of early stage CKD and disease progression using the nanosensor array.

FIGS. 2A-2B. Distinction between early and advanced CKD using a single GNP sensor.

FIGS. 3A-3B. Distinction between early and advanced CKD using a single sensing feature of a GNP sensor.

FIG. 4. CKD specific variations in chemical composition of the breath. Changes in abundance of the identified VOCs that occur in >75% of the breath samples (Table 7). The columns and error bars represent the mean abundance and standard error of mean (SEM), respectively.

DETAILED DESCRIPTION OF THE INVENTION

The present invention provides a method of diagnosing, staging or monitoring CKD using at least one sensor comprising gold nanoparticles capped with specific organic coatings.

WO 2010/064239 to one of the inventors of the present invention discloses a system comprising an array of sensors of single-walled carbon nanotubes (SWCNTs) coated with functionalized oligomers or polymers for measuring VOCs as biomarkers for diagnosis, prognosis and monitoring of renal insufficiencies including, acute renal failure and chronic renal failure. WO 2010/064239 further provides the combination of sensors of SWCNTs coated with functionalized oligomers or polymers with chemiresistive molecularly modified gold nanoparticles and the use of Au nanoparticles coated with 11-mercapto-1-undecanol for the detection of chronic renal failure and acute renal failure, respectively. WO 2010/079490 and WO 2009/066293 to one of the inventors of the present invention disclose sensor apparatus based on 2D films or 3D assemblies of conductive nanoparticles capped with an organic coating for various applications. The present invention now discloses for the first time that gold nanoparticles coated with an organic coating selected from 2-ethylhexanethiol, tert-dodecanethiol, hexanethiol and dibutyl disulfide provide unexpectedly superior results in detecting and staging CKD.

The present invention provides a sensor or a system comprising an array of sensors of organically functionalized gold nanoparticles, particularly suitable for the diagnosis, staging or monitoring of CKD.

According to one embodiment, the sensor comprises gold nanoparticles capped with an organic coating selected from 2-ethylhexanethiol, tert-dodecanethiol, hexanethiol and dibutyl disulfide. Each possibility represents a separate embodiment of the present invention. According to the principles of the present invention, the sensor is sensitive to at least one volatile organic compound present in an exhaled breath sample, said VOC or its level in the exhaled breath sample is being indicative of chronic kidney disease. In certain embodiments, the sensor of the present invention provides the detection of at least one volatile organic compound that is indicative of chronic kidney disease with sensitivity below one part per million (ppm). In other embodiments, the sensor of the present invention provides the detection of at least one volatile organic compound that is indicative of chronic kidney disease with sensitivity of less than 10 parts per billion (ppb). In further embodiments, the sensor of the present invention provides the detection of at least one volatile organic compound that is indicative of chronic kidney disease with sensitivity of 1-5 parts per billion (ppb).

Sensors comprising gold nanoparticles capped with organic coatings can be synthesized as is known in the art, for example using the two-phase method (Brust et al., J. Chem. Soc. Chem. Commun., 801, 2, 1994) with some modifications (Hostetler et al., Langmuir, 14, 24, 1998). Capped gold nanoparticles can be synthesized by transferring AuCl$_4^-$ from aqueous HAuCl.xH$_2$O solution to a toluene solution by the phase-transfer reagent TOAB. After isolating the organic phase, excess thiols are added to the solution. The mole ratio of thiol:HAuCl.xH$_2$O can vary between 1:1 and 10:1, depending on the thiol used. This is performed in order to prepare mono-disperse solution of gold nanoparticles in average sizes of about 2-5 nm. Exemplary procedures include, but are not limited to, thiol:Au mole ratios of 10:1 and 1:1 for dodecanethiol and hexanethiol-capped gold nanoparticles, respectively having an average size of 5 nm. After vigorous stirring of the solution, aqueous solution of the reducing agent NaBH$_4$ in large excess is added. The reaction is constantly stirred at room temperature for at least 3 hours to produce a dark brown solution of the thiol-capped Au nanoparticles. The resulting solution is further subjected to solvent removal in a rotary evaporator followed by multiple washings using ethanol and toluene. Gold nanoparticles capped with dibutyl disulfide can be synthesized by transferring AuCl$_4^-$ from aqueous HAuCl.xH$_2$O solution to a toluene solution by the phase-transfer reagent TOAB. After isolating the organic phase, excess thiols are added to the solution. The mole ratio of dibutyl disulfide:HAuCl.xH$_2$O can vary between 1:1 and 10:1.

The gold nanoparticles of the present invention may have any desirable morphology including, but not limited to, a cubic, a spherical, and a spheroidal morphology. Each possibility represents a separate embodiment of the present invention. In some embodiments, the gold nanoparticles have a spherical morphology with diameters ranging from about 2 nm to about 5 nm.

The synthesized nanoparticles can then be assembled (e.g. by a self-assembly process) to produce a film of capped nanoparticles. The term "self-assembly" as used herein refers to a process of the organization of molecules without intervening from an outside source. The self-assembly process occurs in a solution/solvent or directly on the solid-state substrate. The term "film", as used herein, corresponds to a configuration of well-arranged assembly of coated gold nanoparticles. 2D or 3D films of coated nanoparticles may also be used.

Exemplary methods for obtaining well-ordered two or three dimensional assemblies of coated nanoparticles include, but are not limited to,
  i. Random deposition from solution of coated nanoparticles on solid surfaces. The deposition is performed by drop casting, spin coating, spray coating and other similar techniques as is known in the art.
  ii. Field-enhanced or molecular-interaction-induced deposition from solution of coated nanoparticles on solid surfaces.
  iii. Langmuir-Blodgett or Langmuir-Schaefer techniques. The substrate is vertically plunged through self-organized/well-ordered 2D monolayer of coated nanoparticles at the air-subphase interface, wherein the 2D monolayer of coated nanoparticles is being subsequently transferred onto it. Multiple plunging of the substrate through the 2D monolayer of coated nanoparticles at the air-subphase interface, results in the fabrication of the 3D-ordered multilayers of coated nanoparticles.
  iv. Soft lithographic techniques, such as micro-contact printing (mCP), replica molding, micro-molding in capillaries (MIMIC), and micro-transfer molding (mTM). These methods are based on variations of self-assembly and replica molding of organic molecules and polymeric materials, for fabricating coated nanoparticles from nanometer-scale to a mesoscopic scale (Zhao et al., J. Mater. Chem. 7, 1069-1074, 1997).
  v. Various combinations of Langmuir-Blodgett or Langmuir-Schaefer methods with soft lithographic techniques can be used to produce patterned Langmuir-Blodgett films of molecularly modified coated nanoparticles which are transferred onto solid substrates.
  vi. Printing on solid-state or flexible substrates using an inject printer designated for printed electronics. A solution containing the coated nanoparticles is used as a filling material (or "ink") of the printing head according to procedures well known in the art.

The sensors of the present invention can be configured as any one of the various types of electronic devices, including, but not limited to, capacitive sensors, resistive sensors, impedance sensors, field effect transistor sensors, and the like, or combinations thereof. Each possibility represents a separate embodiment of the present invention. In one embodiment, the sensors are configured as chemiresistors.

In some embodiments, the present invention provides a system comprising a plurality of sensors (at least two sensors), each sensor comprising gold nanoparticles capped with an organic coating selected from 2-ethylhexanethiol, tert-dodecanethiol, hexanethiol and dibutyl disulfide. In one embodiment, the system comprises four sensors comprising a sensor comprising gold nanoparticles capped with 2-ethylhexanethiol, a sensor comprising gold nanoparticles capped with tert-dodecanethiol, a sensor comprising gold nanoparticles capped with hexanethiol and a sensor comprising gold nanoparticles capped with dibutyl disulfide. In another embodiment, the system comprises three sensors comprising a sensor comprising gold nanoparticles capped with 2-ethylhexanethiol, a sensor comprising gold nanoparticles capped with hexanethiol and a sensor comprising gold nanoparticles capped with dibutyl disulfide. In yet another embodiment, the system comprises two sensors comprising a sensor comprising gold nanoparticles capped with 2-ethylhexanethiol and a sensor comprising gold nanoparticles capped with tert-dodecanethiol. It will be recognized by one of skill in the art that the selection of sensors is performed so as to enable the desired sensitivity to diagnose or monitor a particular stage of CKD. In certain embodiments, the sensors of the present invention further comprise one or more conducting elements. The conducting elements may include a source and a drain electrode separated from one another by a source-drain gap. The system disclosed herein may further comprise a gate electrode wherein the sensor signal may be indicative of a certain property of the nanoparticles under the influence of a gate voltage.

According to the principles of the present invention, the system comprises a detection means for detecting the signal upon exposure of the sensor/s to at least one VOC indicative of CKD. The sensor signal may be induced by a change in any one or more of conductivity, resistance, impedance, capacitance, inductance, or optical properties of the sensor/s upon exposure to said VOC(s). Changes in the optical properties of the sensor/s can be measured using e.g., spectroscopic ellipsometry. Suitable detection means include, but are not limited to, devices which are susceptible to a change in any one or more of resistance, conductance, alternating current (AC), frequency, capacitance, impedance, inductance, mobility, electrical potential, an optical property and voltage threshold. Each possibility represents a separate embodiment of the present invention. In additional embodiments, the detection means includes devices which are susceptible to swelling or aggregation of nanoparticles as well as devices which are susceptible to a change in any one or more of optical signal, florescence, chemiluminsence, photophorescence, bending, surface acoustic wave, piezoelectricity and the like. Each possibility represents a separate embodiment of the present invention.

In some embodiments, the sensing signal is obtained through the adsorption of at least one volatile organic compounds that is indicative of CKD on the coated nanoparticles. According to the principles of the present invention, the signal is generated by the change in conformation or structure of the film/assembly of coated nanoparticles upon VOC adsorption. The present invention thus provides the direct sensing of the VOC that is indicative of CKD through its adsorption on the film/assembly of coated nanoparticles.

According to the principles of the present invention, the system comprising a plurality of sensors further comprises a processing unit comprising a pattern recognition analyzer, wherein the pattern recognition analyzer receives sensor output signals and analyses them by various pattern analysis algorithms to produce an output signature. By comparing an unknown signature with a database of stored or known signatures, VOCs indicative of CKD can be identified. The analyzer utilizes learning and pattern recognition algorithms comprising artificial neural networks, support vector machine (SVM), multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART) and statistical methods such as principal component analysis (PCA), partial least squares (PLS), multiple linear regression (MLR), principal component regression (PCR), discriminant function analysis (DFA) including linear discriminant analysis (LDA), and cluster analysis including nearest neighbor. Each possibility represents a separate embodiment of the present invention. In an exemplary embodiment, the algorithm used for processing the data is an artificial neural network algorithm. In another exemplary embodiment, the algorithm used for processing the data is support vector machine (SVM).

Support Vector Machine (SVM) performs classification by constructing an N-dimensional hyperplane that optimally separates the data into two categories. SVM models are closely related to neural networks. Using a kernel function, SVM models are alternative training methods for polynomial, radial basis function and multi-layer perceptron classifiers in which the weights of the network are derived by solving a quadratic programming problem with linear constraints, rather than by solving a non-convex, unconstrained minimization problem as in standard neural network training. Using an SVM model with a sigmoid kernel function is equivalent to a two-layer, perceptron neural network.

Using the SVM model, a predictor variable is called an attribute, and a transformed attribute that is used to define the hyperplane is called a feature. The task of choosing the most suitable representation is known as feature selection. A set of features that describes one case (i.e., a row of predictor values) is called a vector. The output of SVM modeling provides the optimal hyperplane that separates clusters of vectors in a manner that affords cases with one category of the target variable on one side of the plane and cases with the other category on the other size of the plane. The vectors near the hyperplane are the support vectors.

Additional algorithms suitable for identifying patterns of VOCs indicative of CKD include, but are not limited to, Fisher linear discriminant analysis (FLDA), soft independent modeling of class analogy (SIMCA), K-nearest neighbors (KNN), neural networks, genetic algorithms, and fuzzy logic algorithms. Each possibility represents a separate embodiment of the present invention. In some embodiments, the Fisher linear discriminant analysis (FLDA) and canonical discriminant analysis (CDA) and combinations thereof are used to compare the output signature and the available data from the database. After analysis is completed, the resulting information can be displayed on a display or transmitted to a host computer.

The present invention further provides a method of diagnosing, staging and monitoring CKD in a subject using the sensor or system of the present invention. The sensor or array of sensors is exposed to a test exhaled breath sample and a signal or a plurality of signals each comprising at least one response induced parameter is measured by a detection means. The obtained signal may be analyzed as is. In accordance with these embodiments, the signal is analyzed by comparing it to the response from a control sample whereby a significantly different response of the test sample as compared the control sample is indicative of CKD or its stage.

Alternatively, the signal may be analyzed using a pattern recognition algorithm. In accordance with these embodiments, the plurality of signals (or plurality of response induced parameters, i.e. features) forms a response pattern. The response pattern is compared to the response pattern obtained from a control sample (which can be stored in a database) whereby a significantly different response pattern of the test sample as compared the control sample is indicative of CKD or its stage. Further embodiments provide the discrimination between a subject having CKD and a subject having acute renal failure or a subject having end stage renal disease, as well as the discrimination between a subject having early stage CKD (stages 2-3), a subject having advanced CKD (stage 4) and a subject having end stage renal disease (stage 5).

In particular embodiments, the response induced parameters are selected from the group consisting of steady state normalized response, the time interval for obtaining steady state normalized response, and the time required to reach baseline after removal of the test sample. Each possibility represents a separate embodiment of the present invention.

In exemplary embodiments, the response induced parameters are selected from the group consisting of full non-steady state response at the beginning of the signal, full non-steady state response at the beginning of the signal normalized to baseline, full non-steady state response at the middle of the signal, full non-steady state response at the middle of the signal normalized to baseline, full steady state response, full steady state response normalized to baseline, area under non-steady state response, area under steady state response, the gradient of the response upon exposure to the test sample, the gradient of the response upon removal of the test sample, the time required to reach a certain percentage of the response, such as the time required to reach 10%, 20%, 30%, 40%, 50%, 60%, 70%, 80%, 90% or 100% of the response upon exposure to the test sample, and the time required to reach a certain percentage of the response, such as the time required to reach 100%, 90%, 80%, 70%, 60%, 50%, 40%, 30%, 20% or 10% of the response upon removal of the test sample. Each possibility represents a separate embodiment of the present invention.

The term "significantly different" as used herein refers to a statistically significant quantitative difference between the response/response pattern of the test samples and the response/response pattern of a control sample. According to the principles of the present invention, wherein a statistically significant difference in the levels of at least one VOC that is indicative of CKD exists between a test sample and a control sample, the diagnosis monitoring or staging of chronic kidney disease is obtained. A statistically significant difference can be determined by any test known to the person skilled in the art. Common tests for statistical significance include, among others, t-test, ANOVA1 Kruskal-Wallis, Wilcoxon, Mann-Whitney and odds ratio. Individual samples (of unknown status) can be compared with negative control samples obtained from subjects who are not afflicted with CKD. A statistically significant elevation or reduction in the particular response parameter being measured between the test and control sample qualifies as significant difference. A set of control samples can be stored as a reference collection for multiple analyses. In additional embodiments, the unknown test sample may be compared to a sample obtained from a subject known to be affricated with acute renal failure or end stage renal disease. In accordance with these embodiments, a significantly different response or response pattern as compared to the control response/response pattern will be classified as is known in the art.

The method of the present invention may further comprise the step of concentrating the test exhaled breath sample prior to the measurement using a breath concentrator and/or a dehumidifying unit.

Breath pre-concentrators that are within the scope of the present invention include, but are not limited to, I. Solid Phase Microextraction (SPME)—The SPME technique is based on a fiber coated with a liquid (polymer), a solid (sorbent), or a combination thereof. The fiber coating extracts the compounds from the sample either by absorption (where the coating is liquid) or by adsorption (where the coating is solid). The SPME fiber is then inserted directly into the sensing apparatus for desorption and subsequent analysis (Ouyang, et al., Anal. Bioanal. Chem., 386, 1059-1073, 2006; and Coelho et al., J. Chromatography B, 853, 1-9, 2007). Suitable SPME fibers include, but are not limited to, divinylbenzene, carboxen, and polydimethylsiloxane fibers. Each possibility represents a separate embodiment of the present invention.

II. Sorbent Tubes—Sorbent tubes are typically composed of glass and contain various types of solid adsorbent material (sorbents). Commonly used sorbents include, but are not limited to, activated charcoal, silica gel, and organic porous polymers such as Tenax and Amberlite XAD resins. Sorbent tubes are attached to air sampling pumps for sample collection. A pump with a calibrated flow rate in ml/min draws a predetermined volume of air through the sorbent tube. Chemicals are trapped onto the sorbent material throughout the sampling period. This technique was developed by the U.S. National Institute for Occupational Safety and Health (NIOSH).

III. Cryogenic Condensates—Cryogenic condensation is a process that allows recovery of volatile compounds for reuse. The condensation process requires very low temperatures so that the volatile compounds can be condensed. Traditionally, chlorofluorocarbon (CFC) refrigerants have been used to induce condensation. Currently, liquid nitrogen is used in the cryogenic (less than −160° C.) condensation process.

A dehumidifier that is within the scope of the present invention includes, but is not limited to, I. A device which draws moist air over cold refrigerated coils—using this approach, the air moisture condenses into droplets as it passes through cold refrigerated coils into a container. "Dried" air is then brought to its original temperature and returned to the sensing apparatus.

II. Silica Gel—is an amorphous form of silicon dioxide, which is synthetically produced in the form of hard irregular granules or beads. A microporous structure of interlocking cavities provides a very high surface area (800 square meters per gram). This unique structure renders the silica gel as a high capacity desiccant. Water molecules adhere to the surface of the silica gel due to its low vapor pressure as compared to the surrounding air. When pressure equilibrium is reached, the adsorption ceases. Thus, the higher the humidity of the surrounding air, the larger the amount of water that is adsorbed before equilibrium is reached. Silica gel is advantageous as a drying substance since the process of drying requires no chemical reactions and no by products or side effects are produced.

III. Activated carbon—is formed by processing charcoal to an extremely porous carbon substance. Due to its high degree of microporosity, the activated carbon possesses a very large surface area available for chemical reactions. Sufficient activation may be obtained solely from the high surface area, though further chemical treatments often enhance the adsorbing properties of the material.

IV. Desiccant Molecular Sieves—are synthetically produced, highly porous crystalline metal-alumino silicates. They are classified by the many internal cavities of precise diameters, namely, 3 Å, 4 Å, 5 Å, and 10 Å. Adsorption occurs only when molecules to be adsorbed have smaller diameters than the cavity openings. Molecules of high polarity are better adsorbed into the molecular sieves. Molecular sieves adsorb water molecules and other contaminants from liquids and gases down to very low levels of concentrations, often to 1 ppm.

The method of the present invention enables the detection of a single VOC as well as the detection of a plurality of VOCs as CKD breath biomarkers and the unique pattern of these biomarkers which characterizes CKD. In certain embodiments, the VOCs that are indicative of CKD include, but are not limited to, at least one of ethylene glycol, acetoin, styrene, toluene, isoprene, acetone, 2,2,6-trimethyl-octane, 2-butanone, and 2,4-dimethyl-heptane. Each possibility represents a separate embodiment of the present invention.

As used herein and in the appended claims the singular forms "a", "an," and "the" include plural references unless the content clearly dictates otherwise. Thus, for example, reference to "an organic coating" includes a plurality of such organic coatings and equivalents thereof known to those skilled in the art, and so forth. It should be noted that the term "and" or the term "or" is generally employed in its sense including "and/or" unless the content clearly dictates otherwise.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1

Test Population and Breath Collection

A cross-sectional comparative survey between patients attending the out-patient clinic at the Department of Nephrology, Rambam Health Care Campus (Haifa, Israel) and healthy controls (recruited from their accompanying persons) was performed. 62 volunteers at the ages of 22-83 having sufficient clinical and biochemical data were included as the test population (Table 1). The volunteers were recruited after written informed consent. The biochemical data was obtained from standard blood tests less than a month prior to breath testing. All subjects refrained from smoking and drinking coffee for 1 hour prior to breath sampling. The test population was categorized as follows: 22 patients with early (stages 2-3) CKD, 20 patients with advanced (stages 4-5) CKD and 20 healthy controls. The patients were under observation and were given medical treatment (converting enzyme inhibitors; angiotensin receptor blockers; calcium channel blockers; diuretics). None of the patients received dialysis treatment or renal transplantation during breath testing. The patients were staged according to the estimated glomerular filtration rate (eGFR)

that was calculated from plasma creatinine levels, considering patient's age and gender using the Modification of Diet in Renal Disease (MDRD) equation (NKF KDOQI GUIDELINES, 2002;

Levey et al., Kidney Int. 67(6), 2089-2100, 2005; and Collins et al., Kidney Int. Suppl. 87, S24-S31, 2003). Ethical approval was obtained from the Rambam Healthcare Campus and Technion's committee for supervision of human experiments, Haifa, Israel, and the clinical trial was performed according to their guidelines and was registered at Clinicaltrials.gov (registration no.: NCT01274169). Alveolar breath was collected, using an 'offline' method that effectively separated the endogenous from the exogenous breath volatile biomarkers, and excluded the nasal entrainment. The method is described in details in Peng et al., Nano Lett. 8(11), 3631-3635, 2008 and Peng et al., Nature Nanotechnol. 4(10), 669-673, 2009; the content of each of which is hereby incorporated in its entirety.

TABLE 1

Clinical and biochemical variables of tested patients and healthy controls.

|  | Healthy (n = 20) | Stage-2 (n = 6) | Stage-3 (n = 16) | Stage-4 (n = 12) | Stage-5 (n = 8) |
| --- | --- | --- | --- | --- | --- |
| Estimated GFR (ml/min per 1.73 m$^2$)[1] | >120 | 60-90 | 30-59 | 15-29 | ≤15 |
| Gender (% males) | 55 | 100 | 75 | 66 | 100 |
| Average Age ± SD[2] | 45.8 ± 16 | 40.6 ± 19.3 | 54 ± 11.75 | 63.4 ± 9 | 66.3 ± 14.6 |
| Smoking History (current/Ex/never) | 1/0/19 | 2/1/3 | 2/1/13 | 2/1/9 | 1/1/6 |
| Diabetes Mellitus | 2(10%) | 0 | 6 (37%) | 8(66%) | 5(62%) |
| Arterial Hypertension | 7(35%) | 5(83%) | 14(87%) | 11(91%) | 7(87%) |
| Body Weight (kg) | 75.2 ± 15 (45-110) | 70.6 ± 8 (63-86) | 82.3 ± 16 (60-111) | 81.8 ± 18.3 (55-120) | 83.2 ± 20.6 (53-120) |
| Serum Creatinine concentration (mg/dL) | 0.7-1.1[3] | (1.19-1.5) | (1.32-2.65) | (2-3.8) | (4.43-7) |
| Potassium (mEq/L) | 3.5-5.1[3] | 4.7 ± 0.8 | 4.7 ± 0.6 | 4.8 ± 0.5 | 5.1 ± 0.6 |
| Calcium (mg/dL) | 8.5-10.5[3] | 9.9 ± 0.1 | 9.3 ± 0.4 | 9.8 ± 0.3 | 9.0 ± 0.1 |
| Phosphorous (mg/dL) | 2.5-5.0[3] | 3.2 ± 0.4 | 3.9 ± 0.5 | 4.2 ± 0.6 | 4.9 ± 0.6 |

[1]Estimated according to Modification of diet in renal disease (MDFR) formula
[2]SD: Standard Deviation
[3]Nominal values Example 2

Breath Analysis Using the Sensor Array of the Present Invention

The breath samples were tested using the sensor array of the present invention. The array was composed of four cross-reactive chemiresistors that were based on four types of spherical monolayer coated gold nanoparticles (GNPs) with a core diameter of 3-4 nm (Tisch et al., Rev. Chem. Eng. 26, 171-179, 2011; WO 2010/079490, the content of each of which is hereby incorporated in its entirety). The organic ligands that were used as coating: 2-ethylhexanethiol (sensor 1: S1), tert-dodecanethiol (sensor 2: S2), hexanethiol (sensor 3: S3), and dibutyl disulfide (sensor 4: S4). The GNPs were synthesized as described in Dovgolevsky at al., Small 4(11), 2059-2066, 2008; Dovgolevsky at al., Small 5(10), 1158-1161, 2009; Dovgolevsky at al., J. Phys. Chem. C 114(33), 14042-14049, 2010; and Tisch et al., MRS Bull. (35), 797-803, 2010, the content of each of which is hereby incorporated in its entirety.

GNP chemiresistive layers were formed by dispersing the GNPs in chloroform using sonication and drop-casting the solution onto microelectronic transducers. While still coated with solution, the substrate was blown dry with nitrogen. This process was repeated several times to yield a desired resistance of about 1 MΩ. The device was dried for 2 hours at ambient temperature and then baked at 50° C. in a vacuum oven overnight. The microelectronic transducers contained ten pairs of circular interdigitated gold electrodes that were deposited by an electron-beam evaporator TFDS-870 (Vacuum Systems & Technologies) on a piece of device quality silicon wafer capped with 300 nm thermal oxide (Silicon Quest International). The outer diameter of the circular electrode area was 3 mm, and the gap between two adjacent electrodes and the width of each electrode were 20 μm each.

Twenty (20) different GNP sensors were mounted on a custom PTFE circuit board inside a stainless steel test chamber with a volume of 100 cm$^3$. The sampling system delivered pulses of breath to the sensors. The chamber was evacuated between exposures. An Agilent Multifunction switch 34980 was used to measure the resistance as a function of time. Typically, the sensors' responses were recorded for 5 min in vacuum, followed by 5 min under breath exposure, followed by another 5 min in vacuum. The cycles were repeated 2-3 times for reproducibility.

Before exposure to the breath samples, the response of each sensor to several representative volatile organic compounds (VOCs) which are normally found in exhaled breath was examined as reported in Peng et al., Nature Nanotechnol. 4(10), 669-673, 2009, the content of which is hereby incorporated in its entirety. The chemiresistive GNP layers rapidly responded and the response was fully reversible to a wide variety of characteristic VOCs which are found in exhaled breath, at different concentration levels ranging from tens of ppbs to hundreds of ppms, while the sensitivity to water was low. Most of the GNP layers showed a detection limit of 1-5 parts per billion (ppb) to key VOCs. The low sensitivity to water indicates that these sensors are particularly suitable for breath testing, since exhaled breath is fully humidified. Different layers that were based on the same type of GNPs showed similar results with ±15% deviations, while the responses of different types of GNPs were distinctly (several-folds) different. Hence, the effect of the GNP type was reproducible and significantly higher than the variations between different devices.

Similar characteristics were obtained when exposing the sensors to the breath samples. The exposure of the GNP sensors to the breath samples resulted in rapid and fully reversible responses. Each sensor showed a characteristic response to all or to a certain subset of VOCs which were found in the exhaled breath samples. CKD-specific breath patterns were obtained from the collective response of several nano-sensors by applying a statistical pattern recognition algorithm (Haick, J. Phys. D 40, 7173-7186, 2007 and Peng et al., Br. J. Cancer 103, 542-551, 2010, the content of each of which is hereby incorporated in its entirety). The signals from a suitable sub-set of the nanosensors were analyzed using support vector machine (SVM) analysis. SVM analysis is a supervised learning method that provides the best separating line between two data sets, through computerized analysis of the sensing signal and automatic choice of the most suitable set of sensing features. It can be used for data classification and pattern recognition. It can further be applied to multi-dimensional data and does not require normal distribution of the data points around the average value (Cortes et al., Mach. Learn. 30(3), 273-297, 1995). SVM is most suitable for analyzing smaller data sets. The sub-populations were compared by building a multi-class classifier based on a linear u-SVC SVM classifier (Hall et al., SIGKDD Explorations 11(1), 10-18, 2009). Several sensing features (response induced parameters) were extracted from the time-dependent response of each sensor. The experimental data was classified using a total of 4-5 features from the nano-sensor array output that were related to the resistance response upon exposure (F1), the area under the response curve (F2), the sensor's response time (F3), and the sensor's relaxation time after ending the exposure (F4). For distinguishing between CKD patients in stages 2-3 and healthy controls, one sensing feature was extracted from S1 (F1) and three mostly independent features were extracted from S2 (F1, F2, and F4). For distinguishing between stage 4 and stage 5 CKD patients, three mostly independent features were extracted from S1 (F2-F4), one feature was extracted from S3 (F2) and one feature was extracted from S4 (F1). The number of input parameters was kept low enough to avoid over-fitting during the SVM analysis. Standard principal component analysis (PCA) was applied in order to visualize the SVM results in three dimensions.

Cross-validation was utilized to evaluate the specificity and sensitivity by randomly dividing each sub-population into two sets, which were then used as a training set and a test set. Cross-validation has a training stage and a test stage—each time creating a new test set that is blinded against the model. The model is built based on the remaining samples, i.e. the training set. The statistics is thus less biased towards any group that is initially selected as the test set. Cross-validation attempts to remove that bias by generating all possible test sets, providing a solid statistical result and making it superior in the case of relatively limited sample size to the choice of fixed training and test sets. All possible combinations of division into test- and training sets were tested and the results were averaged. It is noteworthy that the results were stable against changing the number of folds in the cross-validation.

Example 3

Breath Analysis Using Gas Chromatography Combined with Mass Spectrometry (GC-MS)

The constituent volatile compounds of the collected breath were identified from a representative sub-set of the collected breath samples (5 patients with stage 5 CKD; 10 patients with stage 4 CKD; 15 patients with stage 3 CKD; 5 patients with stage 2 CKD; and 7 healthy controls), using GC-MS (QP 2010 plus; Shimadzu). The GC-MS analysis was preceded by solid phase micro-extraction (SPME) for pre-concentrating the volatile compounds in the breath samples: A manual SPME holder with an extraction fiber was inserted into the Mylar bag for 30 min before being delivered to the GC-MS. Fibers with divinylbenzene/carboxen/polydimethylsiloxane coating were obtained from Sigma-Aldrich. The extracted fiber in the manual SPME holder was inserted into the injector of the GC (direct mode) for thermal desorption at 270° C. The GC oven profile is provided in Table 2. A capillary column RTX-624 6% cyanopropylphenyl (30 m length, 0.25 mm i.d., 1.4 µm thickness, from Restek) was used. Helium was used as the gas carrier and was set to a constant flow rate of 40 cm/sec. Data preprocessing was performed using the open source XCMS package version 1.22.1 for R environment (http/metlin.scripps.edu/download/). The identities of the volatile compounds were determined by a spectral library match. Of note is that the identification of the volatile compounds through spectral library match and retention times is preliminary and requires confirmation through GC-MS analysis of reference substances. However, the comparison between patients was based on compound masses and retention times. Substances identified in the unfiltered hospital air as typical hospital contaminants (2-methyl-2-propanol, ethanol and methyl-isobutyl-ketone) were disregarded.

TABLE 2

GC-MS oven profile.

| Temperature Ramp (° C./min.) | Temperature (° C.) | Hold Time (min.) |
|---|---|---|
| — | 40 | 3 |
| 5 | 115 | 1 |
| 5 | 120 | 1 |
| 5 | 125 | 1 |
| 5 | 130 | 1 |
| 5 | 135 | 1 |
| 7 | 142 | 1 |
| 7 | 149 | 1 |
| 7 | 156 | 1 |
| 10 | 240 | 0 |

Results:

Identification Of Early Stage CKD Using the Nanosensor Array

Figure 1A:
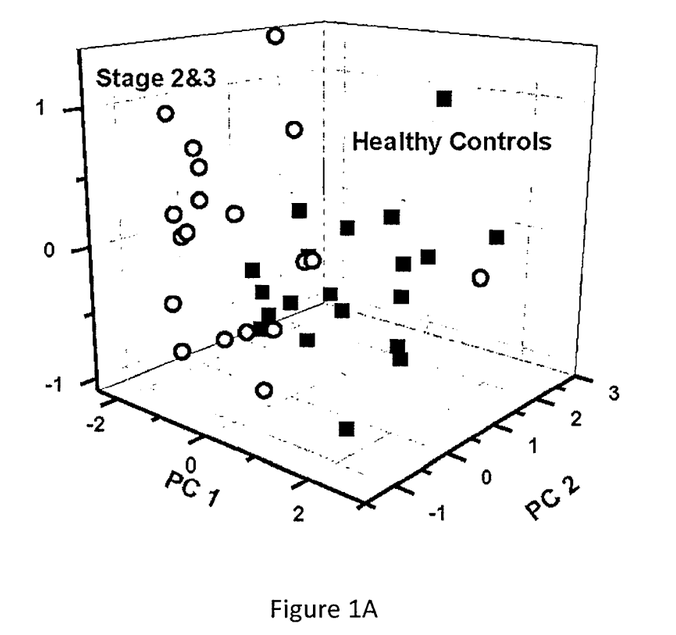
(FIG. 1A) Distinction between early stage CKD (hollow circles) and healthy controls (filled squares) obtained by using 4 sensing features from two sensors (S1 and S2), through SVM analysis. The three-dimensional visualization in principal component space contains 97.52% of the variance of the data.

The feasibility of the designed nanosensor array (Example 2) for diagnosing early stages of CKD was tested by comparing breath samples of 17 patients with CKD at stages 2-3 and breath samples of 15 healthy controls. The two test groups were clearly distinguished through SVM analysis based on four sensing features from two sensors. FIG. 1A shows the SVM results in three-dimensional principal component space. The SVM classification success rate in terms of correct and false classifications was obtained through cross-validation, which allows the estimation of sensitivity (77%), specificity (80%) and accuracy (79%); Table 3. The obtained values for sensitivity, specificity and accuracy provide good diagnosis of CKD at these early stages of the disease.

TABLE 3

The classification success for healthy controls vs. CKD (stages 2-3) estimated through cross-validation.

|  | Classified as stages 2-3 | Classified as healthy |
|---|---|---|
| Stages 2-3 | 17 | 5 |
| Healthy controls | 4 | 16 |

Monitoring CKD Disease Progression Using the Nanosensor Array

Figure 1B:
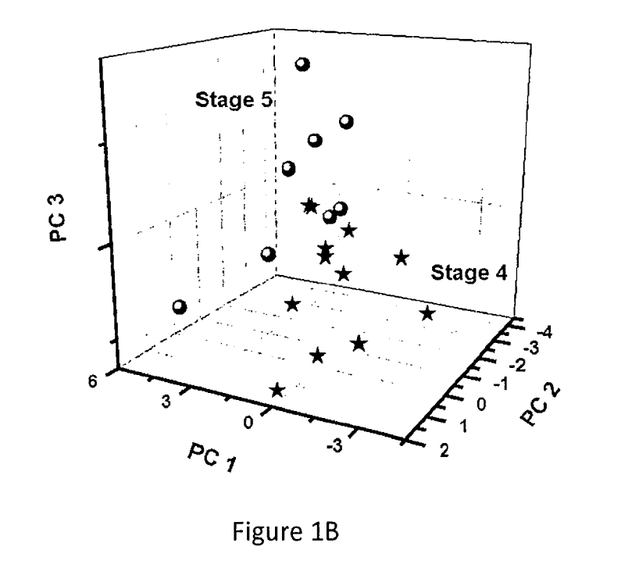
(FIG. 1B) Distinction between advanced CKD (stage 4; stars) and end stage renal disease (stage 5; circles), obtained by using 5 sensing features from three sensors (S1, S3 and S4). The three-dimensional visualization in principal component space contains 99.98% of the variance of the data.

In order to test the ability of the nanosensor array to monitor disease progression, patients with stage 4 CKD were compared to patients with stage 5 CKD. These two stages were compared because a transition between the two stages marks the onset of dialysis treatment. Very good separation between the two states was obtained using five sensing features from three sensors as shown in FIG. 1B. Cross-validation showed that the progression to end stage renal disease could be identified with high sensitivity (75%), specificity (92%) and accuracy (85%); Table 4.

TABLE 4

The classification success for CKD (stage 4) vs. CKD (stage 5) estimated through cross-validation.

|  | Classified as stage 5 | Classified as stage 4 |
|---|---|---|
| Stage 5 | 6 | 2 |
| Stage 4 | 1 | 11 |

Figure 2A:
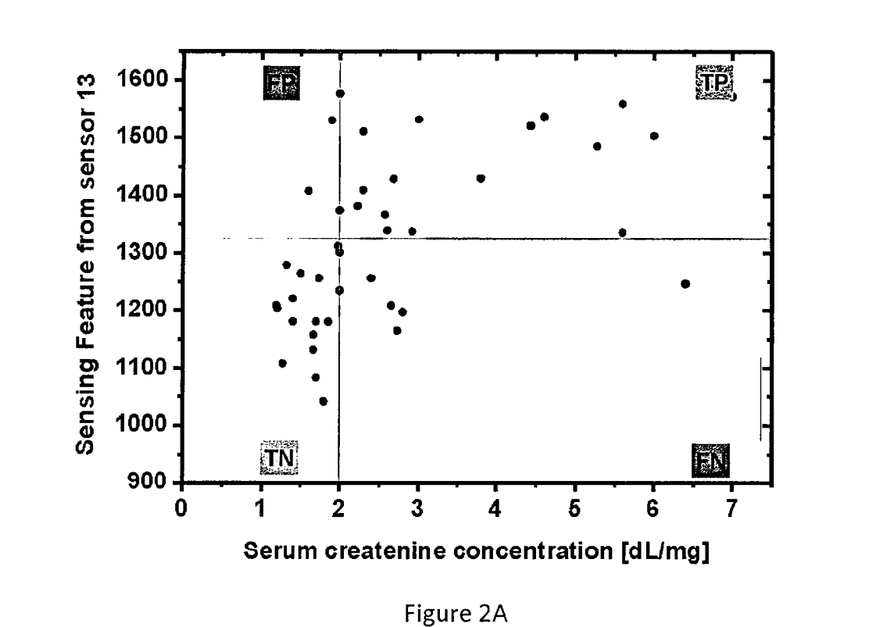
(FIG. 2A) Additive inverse of the resistance response of sensor S1 ($-R_{S1}$) to exhaled patient breath vs. the patients' serum creatinine concentration. The grey line marks the transition between early stage CKD (stages 2-3) and late stage CKD (stages 4-5) at eGFR=30 ml/min per 1.73 m$^2$, corresponding to the sensing cut-off value of 1.33 k$\Omega$.
Figure 2B:
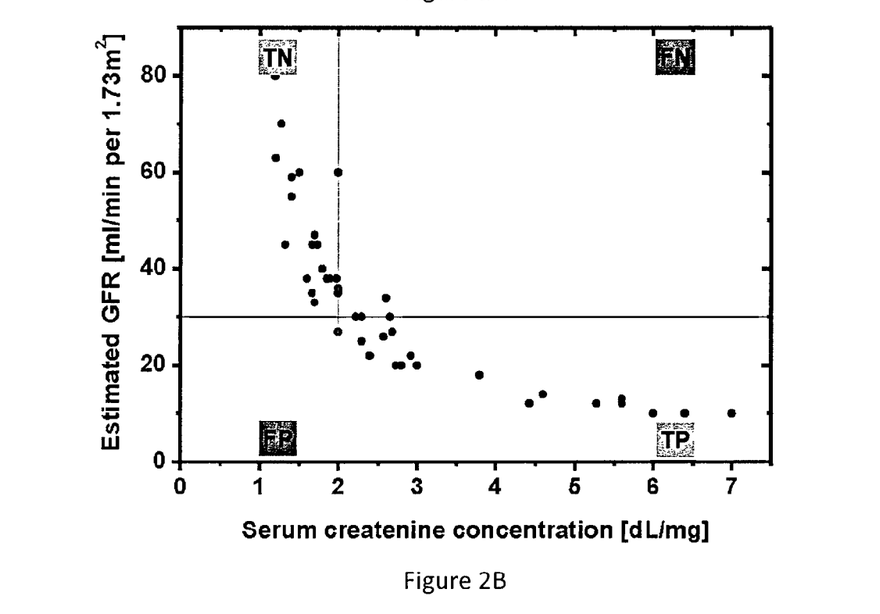
(FIG. 2B) Estimated glomerular filtration rate (eGFR) vs. the patients' serum creatinine concentration. The transition from early-stage to advanced stage CKD and the sensing cut-off are marked by grey lines.
Figure 3A:
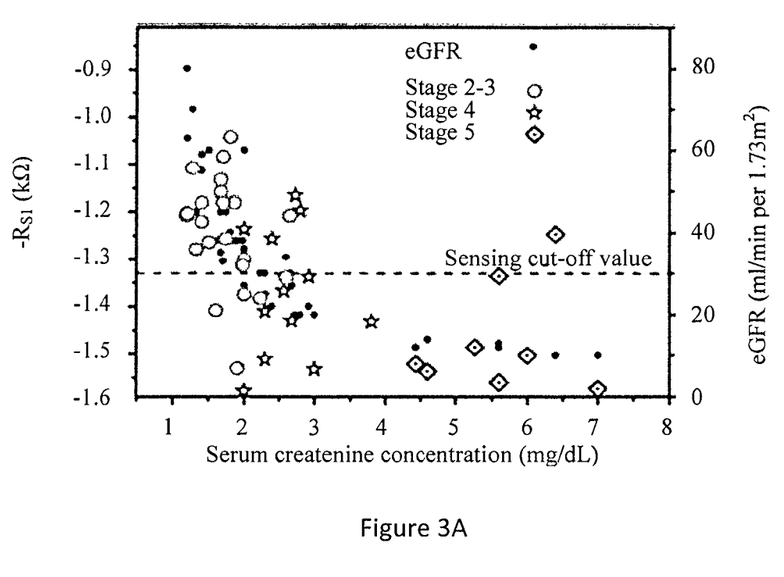
(FIG. 3A)–$R_{S1}$ to exhaled patient breath (stages 2-3: hollow circles; stage 4: stars; and stage 5: diamonds) vs. the patients' serum creatinine concentration. The estimated glomerular filtration rate (eGFR) values are shown for comparison (filled circles).
Figure 3B:
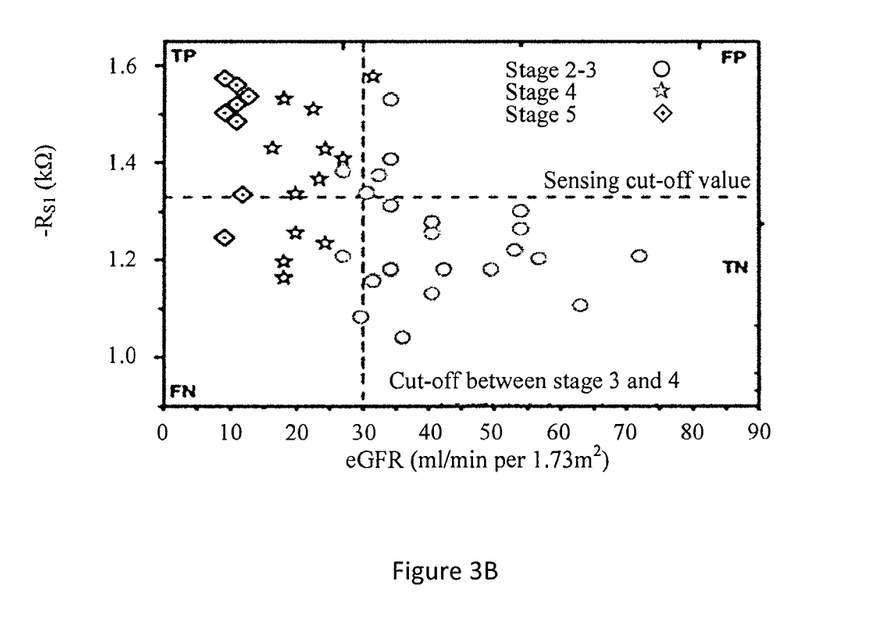
(FIG. 3B) Sensing signal of sensor S1 vs. eGFR (stages 2-3: circles; stage 4: stars; and stage 5: diamonds). The transition from early-stage to late-stage CKD and the sensing cut-off are marked by grey lines.

Several sensing features show statistically significant differences between early stage (stages 2-3) and late stage (stages 4-5) CKD. Because of the strong inter-dependency between the two stages they are not suitable as SVM input variables. FIG. 2A shows, as an example, the resistance response of sensor S1 to the exhaled breath of all tested CKD patients versus their measured plasma creatinine concentration. The scattering is mainly attributed to patient diversity and experimental scattering of the signal readout. The transition from early-stage to late stage CKD is marked by eGFR=30 ml/min per 1.73 m² (see Table 1), corresponding to a sensing signal cut-off value of 1.33 kΩ. These two cut-off values were used to determine the number of true positive (TP), true negative (TN), false positive (FP) and false negative (FN) patient classifications (Table 5). Using this classification, the sensitivity, specificity and accuracy of determining the progression from early to late stage disease with a single sensing feature was estimated as 75%, 77% and 76%, respectively. FIG. 2B shows the estimated eGFR vs. the patients' serum creatinine concentration. FIGS. 3A and 3B show the progression from early-stage to late-stage CKD using a single sensing feature of sensor S1, without the need for statistical analysis. FIG. 3A shows a negative, inverse dependence on creatinine concentration. The inverse creatinine dependence of the eGFR values, which were calculated from the measured creatinine serum concentration, the patient's age and gender using the MDRD equation, is represented in the same graph. Table 6 provides the number of true positive (TP), true negative (TN), false positive (FP) and false negative (FN) patient classifications.

TABLE 5

The classification success for CKD (stage 2-3) vs. CKD (stage 4-5) estimated through cross-validation.

|  | Classified as stage 4-5 | Classified as stage 2-3 |
|---|---|---|
| Stage 4-5 | 18 | 2 |
| Stage 2-3 | 7 | 15 |

TABLE 6

The classification success for CKD (stage 2-3) vs. CKD (stage 4-5).

|  | Classified as stage 4-5 | Classified as stage 2-3 |
|---|---|---|
| Stage 4-5 | 15 | 5 |
| Stage 2-3 | 5 | 17 |

Chemical Analysis of the Breath of CKD Patients

Figure 4:
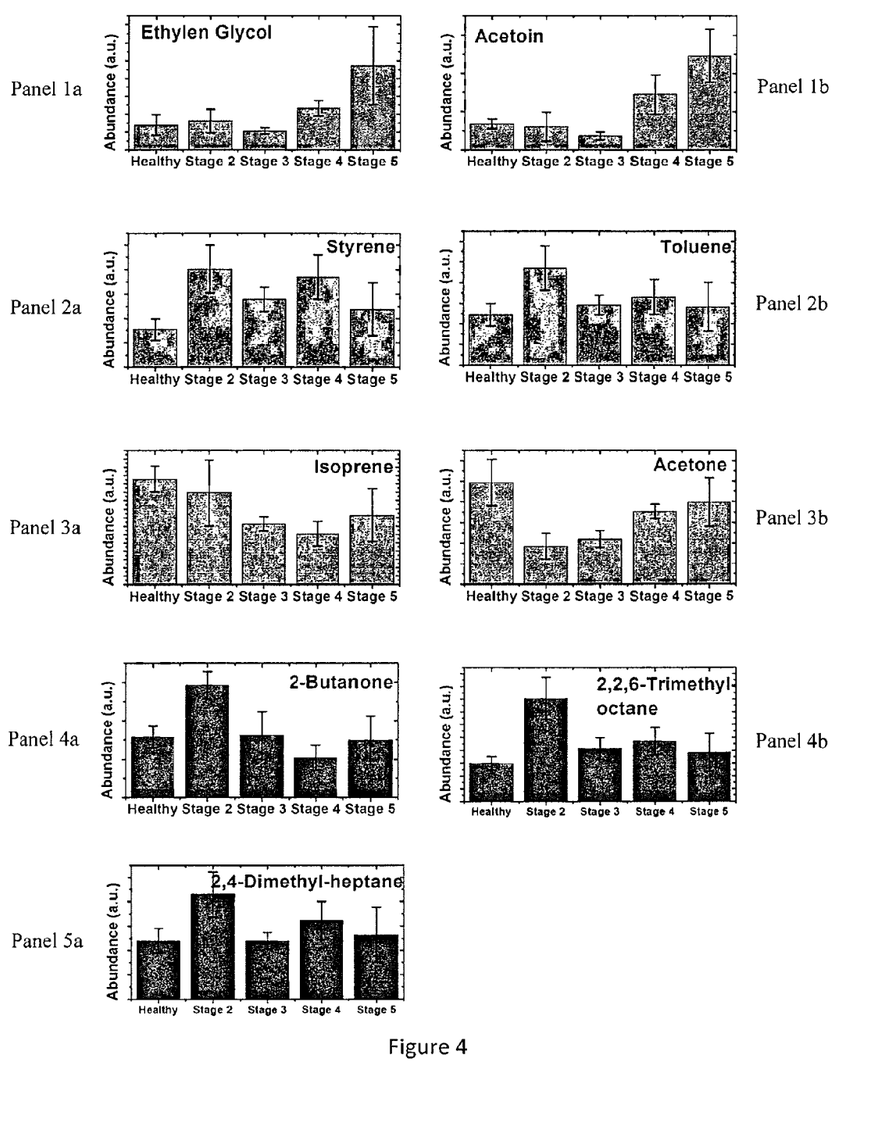

The chemical composition of the exhaled breath of CKD patients was analyzed and compared to the breath of healthy controls, using GC-MS/SPME as described in Example 3. The VOCs that were present in >75% of the breath samples of CKD patients and healthy controls were identified, and their mean abundance with experimental error (standard error of mean; SEM) was calculated. The distinction between the patient sub-populations was studied via Wilcoxon/Kruskal-Wallis tests. Table 7 lists the corresponding p-values. Increase or decrease in abundance are indicated by (+) and (−), respectively. FIG. 4 shows the variations in average abundance that could be observed for nine breath VOCs (ethylene glycol, acetoin, styrene, toluene, isoprene, acetone, 2-butanone, 2,2,6-trimethyl-octane, and 2,4-dimethyl-heptane) which showed statistically significant changes through disease progression. The SEMs are represented by error bars. Six further VOCs that were present in >75% of the CKD and healthy breath samples showed no significant changes (Table 7).

TABLE 7

Changes in chemical composition of the breath during CKD progression.

| | | Significance of the distinction between CKD subpopulations (p-value) | | | | |
|---|---|---|---|---|---|---|
| | Compound name | Healthy vs. stage-2 | Stage-2 vs. stage-3 | Stage-3 vs. stage-4 | Stage-4 vs. stage-5 | Possible origin |
| Group 1 | ethylen glycol | NS | | 0.018 (+) | NS | Sugar cycle metabolite or environmental |

TABLE 7-continued

Changes in chemical composition of the breath during CKD progression.

| | | Significance of the distinction between CKD subpopulations (p-value) | | | | |
|---|---|---|---|---|---|---|
| | Compound name | Healthy vs. stage-2 | Stage-2 vs. stage-3 | Stage-3 vs. stage-4 | Stage-4 vs. stage-5 | Possible origin |
| | acetoin | NS | | 0.005 (+) | NS | toxin Sugar cycle metabolite (diabetes-related) or environmental (food additive, sweetener) |
| Group 2 | styrene | 0.042 (+) | | NS | | Environmental toxins |
| | toluene | 0.028 (+) | | NS | | |
| Group 3 | isoprene | Gradual decrease till stage-3 (healthy vs. stage-3: p = 0.006) | | NS | | Cholesterol cycle and physical activity-related |
| | acetone | Gradual decrease till stage-3 (healthy vs. stage-3: p = 0.018) | | 0.025 (+) | NS | Biomarker related to diabetes |
| Group 4 | 2,2,6-trimethyl-octane | 0.007 (+) | 0.049 (−) | NS | | Potential CKD biomarkers |
| | 2-butanone | 0.028 (+) | 0.013 (−) | NS | | |
| | 2,4-dimethyl-heptane | Sub-signif. increase | 0.033 (−) | NS | | |
| Group 5 | 2-ethylpentane | | | NS | | NS |
| | nonanal | | | NS | | |
| | o-cymene | | | NS | | |
| | 2-methyl-hexane | | | NS | | |
| | 2,2,3-trimethyl-hexane | | | NS | | |
| | m-ethyl-methyl-benzene | | | NS | | |

NS: non-significant changes

The results presented in table 7 show four groups of compounds which represent distinct trends of variations in VOC composition of breath samples. The abundance of ethylene glycol and acetoin remained relatively constant up to stage 3 CKD, and showed a significant increase in stage 4 CKD and a further increase towards stage 5 CKD. The second group of compounds comprises the known industrial toxins styrene and toluene. Both compounds showed a significant increase during early-stage disease (stage 2), reached a plateau during stage 3 and remained relatively constant thereafter. The third group comprises isoprene and acetone, which are present in exhaled breath, usually in large quantities. Both substances decreased during stage 2 CKD and remained relatively constant thereafter. Acetone showed a significant increase in stage 4 CKD, correlating to the expected reduction in hyperfiltration during late stage disease. The fourth group contains two methylated hydrocarbons and a ketone, which showed a significant, brief increase during stage 2 CKD, before their abundance decreased again to the levels observed for the healthy controls. Collectively, these substances could be used as breath biomarkers for early stage disease (e.g. for disease-related oxidative stress). An additional group (Group 5) which contained six compounds that were present in >75% of the CKD and healthy breath samples, but showed no significant increase or decrease that could be related to the disease progression was identified (Table 7). Without being bound by any theory or mechanism of action, the VOC substances which show a distinct trend of variations in patients with CKD vs. healthy controls, could be associated with accumulated environmental toxins, or they could be endogenous biomarkers of CKD-related medical conditions and bodily processes. The identification of early stage CKD and the distinction between patient populations with different CKD stages could stem from the sensing of these VOC substances by the sensor or system of the present invention. Thus, the present invention provides a sensor, system and methods of differentiating between subjects having early-stage CKD and healthy controls, subjects having stage 4 CKD and subjects having and stage 5 CKD, and between subjects having early-stage (stages 2&3) CKD and late-stage (stages 4&5) CKD. Accordingly, the sensor, system and methods of the present invention are useful for the early diagnosis of CKD and the detection of disease progression from early stage to advanced CKD and further to end stage renal disease.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

What is claimed is:

1. A method of diagnosing or staging chronic kidney disease (CKD) in a subject, the method comprising the steps of:
   (a) providing a system comprising a sensor array comprising at least two sensors comprising gold nanoparticles capped with an organic coating selected from the group consisting of 2-ethylhexanethiol, tert-dodecanethiol, hexanethiol and dibutyl disulfide; and a processing unit comprising a pattern recognition algorithm;
   (b) exposing the sensor array to a test exhaled breath sample;
   (c) measuring a plurality of electric signals generated by detection of a plurality of volatile organic compounds (VOCs) indicative of chronic kidney disease and its stages in the test sample by the sensor array, wherein the VOC indicative of stage 2 CKD is selected from the group consisting of toluene, 2,2,6-trimethyl-octane 2-butanone, and combinations thereof; wherein the VOC indicative of stage 2-3 CKD is acetone; wherein the VOCs indicative of probability of stage 4 CKD is selected from the group consisting of ethylene glycol, acetoin and a combination thereof; wherein the VOC indicative of stage 5 CKD is selected from the group consisting of ethylene glycol, acetoin and a combination thereof; and wherein the VOC indicative of subject not afflicted with CKD is styrene, and the plurality of electric signals form a response pattern; and
   (d) analyzing the response pattern obtained in step (c) using the pattern recognition algorithm by comparing the response pattern to stored data obtained from a set of control samples, the set of control samples being obtained from a control subject selected from the group consisting of a person who is not afflicted with CKD, a person known to be afflicted with stage 2 CKD, a person known to be afflicted with stage 3 CKD, a person known to be afflicted with stage 4 CKD, and a person known to be afflicted with stage 5 CKD, thereby providing the diagnosis or staging of chronic kidney disease.

2. The method of claim 1, wherein the gold nanoparticles have a morphology selected from a cubic, a spherical, and a spheroidal morphology.

3. The method of claim 1, wherein each sensor is configured in a form selected from the group consisting of a capacitive sensor, a resistive sensor, a chemiresistive sensor, an impedance sensor, and a field effect transistor sensor.

4. The method of claim 1, wherein the sensor array comprises four sensors of gold nanoparticles capped with an organic coating comprising 2-ethylhexanethiol, tert-dodecanethiol, hexanethiol and dibutyl disulfide.

5. The method of claim 1, comprising measuring a plurality of electric signals generated by detection of each volatile organic compound indicative of chronic kidney disease in the test sample.

6. The method of claim 1, wherein the system further comprises a detection device for measuring the plurality of electric signals, wherein the detection device measures a change in at least one of property of a sensor, selected from the group consisting of resistance, conductance, alternating current (AC), frequency, capacitance, impedance, inductance, electrical potential, and voltage threshold.

7. The system of claim 1, wherein the pattern recognition algorithm is selected from the group consisting of artificial neural network algorithm, support vector machine (SVM), principal component analysis (PCA), multi-layer perception (MLP), generalized regression neural network (GRNN), fuzzy inference system (FIS), self-organizing map (SOM), radial bias function (RBF), genetic algorithm (GAS), neuro-fuzzy system (NFS), adaptive resonance theory (ART), partial least squares (PLS), multiple linear regression (MLR), principal component regression (PCR), discriminant function analysis (DFA), linear discriminant analysis (LDA), cluster analysis, and nearest neighbor.

8. The method of claim 1, further comprising the step of concentrating the test exhaled breath sample prior to step (b) using at least one of a breath concentrator and a dehumidifying unit.

9. The method of claim 1 for differentiating between an unhealthy subject having chronic kidney disease (CKD) and a healthy subject, the method comprising measuring a signal generated by detection of styrene.

10. The method of claim 1 for diagnosing stage 5 CKD in a subject, the method comprising measuring a plurality of signals generated by detection of at least one VOCs selected from ethylene glycol and acetoin.

11. The method of claim 1 for diagnosing stage 2 CKD in a subject, the method comprising measuring a plurality of signals generated by detection of at least one VOC selected from the group consisting of toluene 2,2,6-trimethyl-octane, and 2-butanone.

12. The method of claim 1, comprising measuring a plurality of signals generated by detection of a plurality of VOCs selected from the group consisting of ethylene glycol, acetoin, acetone, styrene, toluene, 2-butanone and 2,2,6-trimethyl-octane.

* * * * *